United States Patent [19]
Wood

[11] 4,367,410
[45] Jan. 4, 1983

[54] WASTE PURIFICATION APPARATUS AND METHOD

[75] Inventor: Myron D. Wood, Hasbrouck Heights, N.J.

[73] Assignee: Pure Water Systems, Inc., Fairfield, N.J.

[21] Appl. No.: 267,039

[22] Filed: May 26, 1981

Related U.S. Application Data

[63] Continuation of Ser. No. 55,593, Jul. 9, 1979, abandoned.

[51] Int. Cl.³ .............................................. A61L 2/10
[52] U.S. Cl. .................................. 250/431; 250/436; 250/437; 250/438; 422/24
[58] Field of Search .......................... 422/24, 186, 23; 250/431, 435, 436, 437, 438, 432 R

[56] References Cited

U.S. PATENT DOCUMENTS

| | | | |
|---|---|---|---|
| 3,182,193 | 5/1965 | Ellner et al. | 422/24 X |
| 3,462,597 | 8/1969 | Young | 422/24 X |
| 3,637,342 | 1/1972 | Veloz | 250/436 |
| 3,837,800 | 9/1974 | Wood | 422/24 |
| 4,103,167 | 7/1978 | Ellner | 250/432 R |

FOREIGN PATENT DOCUMENTS 2213658 10/1973 Fed. Rep. of Germany ........ 422/24

*Primary Examiner*—Barry S. Richman
*Attorney, Agent, or Firm*—Fitzpatrick, Cella, Harper & Scinto

[57] ABSTRACT

A method and apparatus for purifying secondary waste water effluent by ultraviolet radiation, wherein a plurality of ultraviolet lamps are concentrically mounted within support jackets arranged in parallel and which extend transversely across the fluid flow path of the waste water to be treated, adjacent jackets being spaced less than about one half inch apart so that none of the waste water is more than about one quarter inch away from a jacket as it flows past the lamps, and wherein the number of lamps is selected to satisfy the equation:

$$3 \leq X(l)/V \leq 5$$

where X is the number of lamps, l is the usable arc length of the lamps in inches, and V is the volume flow rate in gallons per minute.

12 Claims, 9 Drawing Figures

WASTE PURIFICATION APPARATUS AND METHOD

This is a continuation of application Ser. No. 55,593, filed July 9, 1979 now abandoned.

BACKGROUND OF THE INVENTION

The present invention relates to apparatus and techniques for treating secondary waste water effluent and more particularly to the treatment of such effluent with ultraviolet radiation.

In order to minimize the health hazards associated with the disposal of sewage, it is necessary to adequately disinfect the water before it is fed back into rivers and streams. Conventionally, disinfecting has been done by a subsequent chlorination step; but chlorination leaves residual free chlorine in the effluent and also forms potentially carcinogenic chlorinated hydrocarbons, both of which are unacceptable under present health and ecological standards. While removal of the residual chlorine and some chlorinated compounds is feasible, this additional step substantially increases the overall cost of the sewage treatment. Accordingly alternative purification methods have been sought.

Ozone treatment has been proposed as one alternative of chlorination, but the cost involved is quite prohibitive.

Iodine, bromine and bromine chloride processes are also being tested, but no data for large scale operations is yet available.

It has also long been known that ultraviolet radiation has a pronounced lethal effect on microorganisms and ultraviolet lamps, which emit ultraviolet rays in the range of 2,500 to 2,700 Angstroms, have been used to purify gases and liquids. U.S. Pat. No. 3,182,193 discloses a system for subjecting a fluid to such ultraviolet radiation. However, heretofore, suspended solids and high fluid volume of secondary sewage treatment have prohibited the effective use of ultraviolet radiation.

I have previously discovered that intensity is more effective in obtaining bacterial kill than long dwell time at low intensity. But intensity drops off hyperbolically at the distance from the source of the radiation increases. Therefore, to assure high intensity purification, my earlier U.S. Pat. No. 3,837,800 discloses my "thin film" concept and a device constructed to cause the inlet fluid to assume a sheet-like flow pattern as it is directed sequentially past a row of ultraviolet lamps. While this patent discloses that several such devices may be stacked to increase the flow rate, such arrangement is not readily adaptable for use in commercial sewage treatment plants which are designed to handle millions of gallons of waste water a day.

SUMMARY OF THE INVENTION

The present invention overcomes the disadvantages of the prior art by means of a novel method and apparatus for treating secondary waste water effluent from a commercial sewage treatment plant with ultraviolet radiation. Not only does the present invention avoid the production of potential carcinogens, but is also provides a greater bacterial kill rate, a broader kill range and provides greater clarity of the effluent devoid of residual chlorine than has previously been possible in sewage treatment methods.

According to one aspect of the invention, there is provided an apparatus for treating secondary waste water effluent with ultraviolet light comprising a housing shaped to define a fluid passageway therethrough between an inlet and outlet formed at opposite ends thereof, a plurality of elongated cylindrical, light emitting jackets mounted in parallel within said housing to extend transversely across the fluid passageway, the adjacent jackets being spaced less than about one half inch apart so that none of the waste water is more than one quarter inch away from a jacket as it flows through the housing; a plurality of elongated ultraviolet lamps removably and concentrically mounted within the jackets, wherein the number of lamps and associated jackets satisfies the equation:

$$3 \leq X(l)/V \leq 5$$

where X is the number of lamps, l is the usable arc length of the lamps in inches and V is the volume flow rate of the waste water in gallons per minute; and means for supplying electrical power to operate the ultraviolet lamps.

The apparatus may also be provided with wiping means for simultaneously wiping the outer surfaces of the jackets together with means for reciprocating the wiping means. The wiping means is preferably a plate formed with a plurality of apertures through which the jackets extend and annular wiper glands are provided within each aperture between the plate and associated jacket. The reciprocating means is preferably a pneumatic cylinder housing a reciprocating piston connected by cable to the opposite sides of the wiper plate.

According to a further aspect of the invention there is provided a novel method of treating secondary waste water effluent with ultraviolet light comprising the steps of directing a flow of secondary waste water effluent transversely past a plurality of substantially parallel ultraviolet lamps concentrically mounted in light transmitting support jackets, adjacent support jackets being spaced less than about one half inch apart so that none of the waste water is more than about one quarter inch from a jacket as it passes the lamps, wherein the number of lamps and associated jackets is sufficient to satisfy the equation:

$$3 \leq X(l)/V \leq 5$$

where X is the number of lamps, l is the usable arc length of the lamps in inches and V is the volume flow rate of the waste water in gallons per minute; and treating the effluent with ultraviolet radiation whereby said effluent is disinfected.

There has thus been outlined the more important features of the invention in order that the detailed description thereof that follows may be better understood and in order that the present contribution to the art may be better appreciated. There are, of course, additional features of the invention which will be described hereinafter and which will form the subject of the claims appended thereto. Those skilled in the art will appreciate that this invention may be utilized as a basis for designing other structures and methods for carrying out the several purposes of the invention. It is therefore, important that the claims be regarded as including such equivalent constructions as do not depart from the spirit and scope of the invention.

BRIEF DESCRIPTION OF THE DRAWINGS

A single embodiment of the invention has been chosen for purposes of illustration and description and is shown in the accompanying drawings forming a part of the specification, wherein.

DETAILED DESCRIPTION OF THE PREFERRED EMBODIMENT

Figure 1:
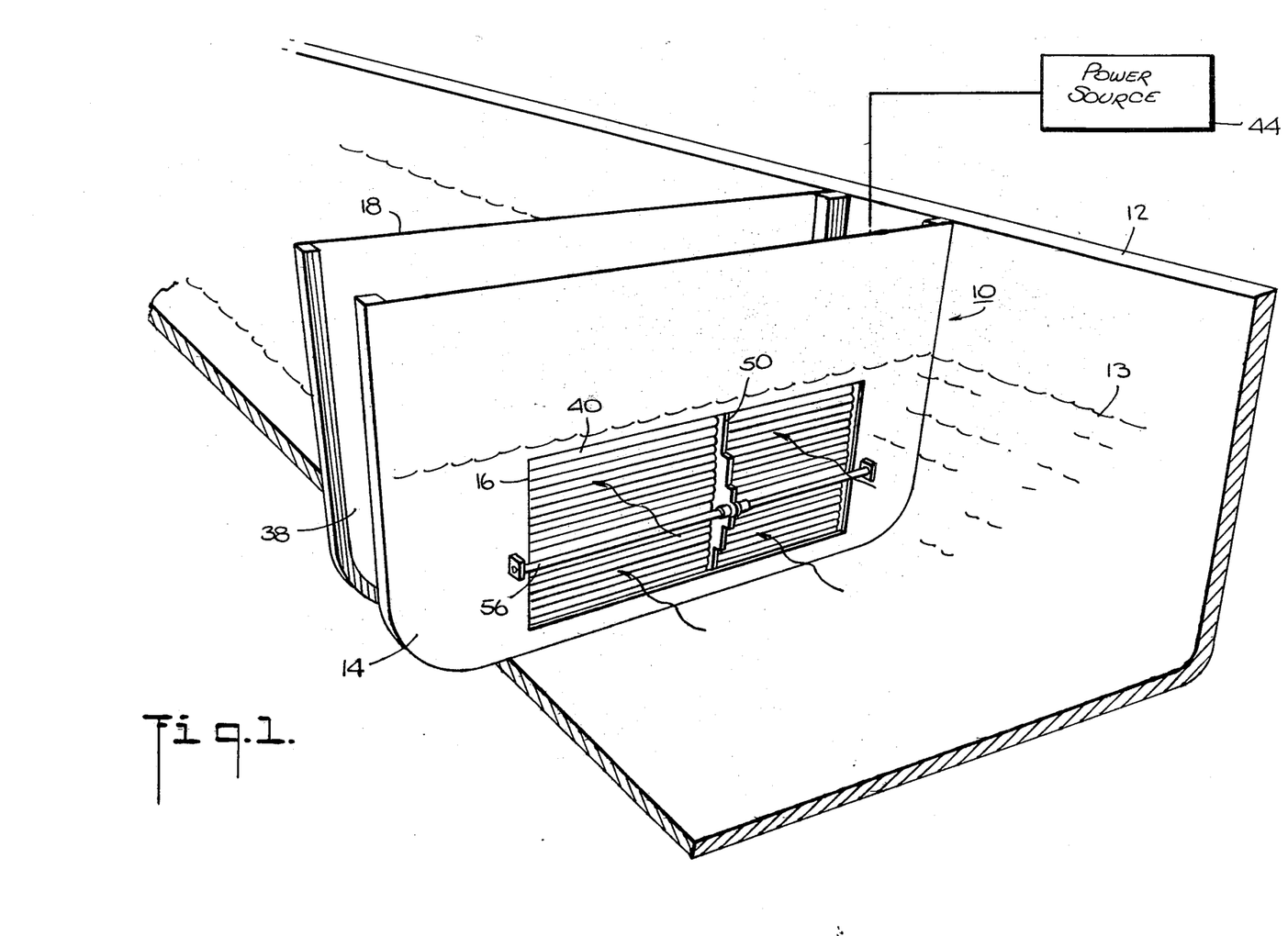
FIG. 1 is a perspective view, partially cut away, of a waste water purification unit constructed according to the present invention, positioned in a channel carrying the effluent from secondary waste water treatment.

With reference to FIG. 1 a waste water purification unit 10 according to my invention is shown positioned across a channel 12, such as a chlorine contact chamber in an existing sewage treatment plant. Typically, means (not shown) are provided for gravitational feed of the secondary waste water effluent 13 through channel 12.

Figure 2:
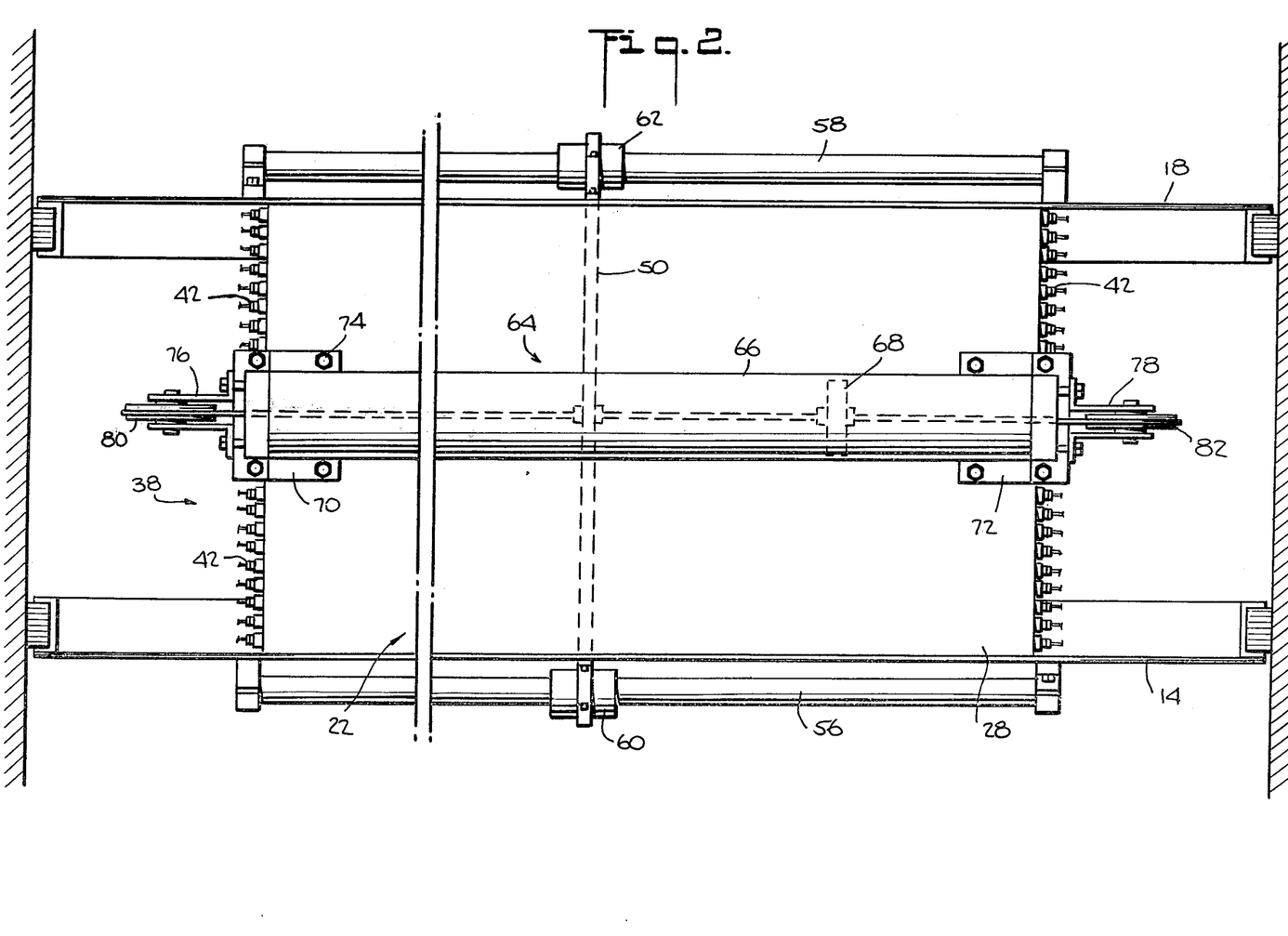
FIG. 2 is a top plan view of the purification unit of FIG. 1.
Figure 4:
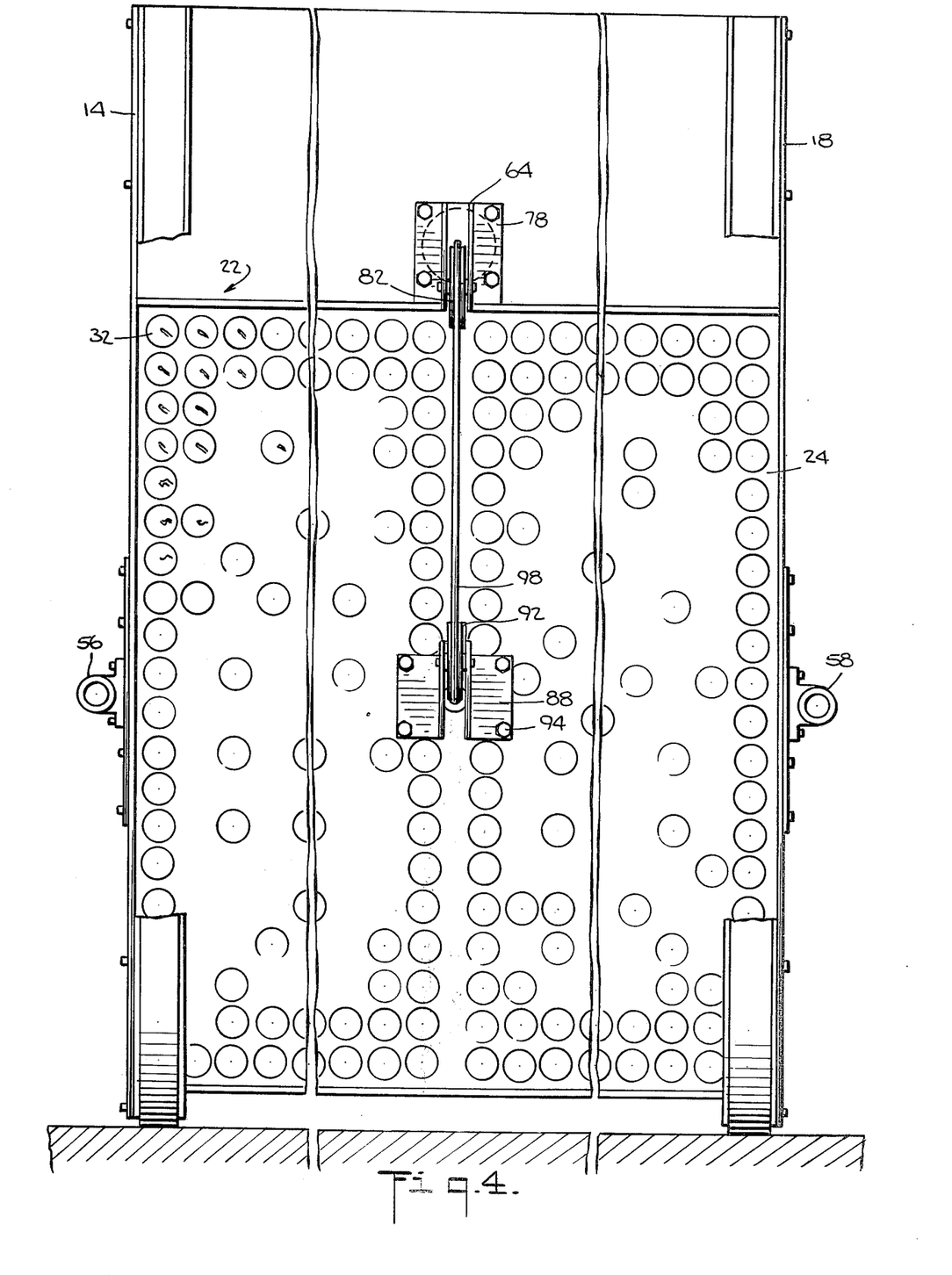
FIG. 4 is an elevational view, partially cut away, showing one side of the unit of FIG. 1.
Figure 5:
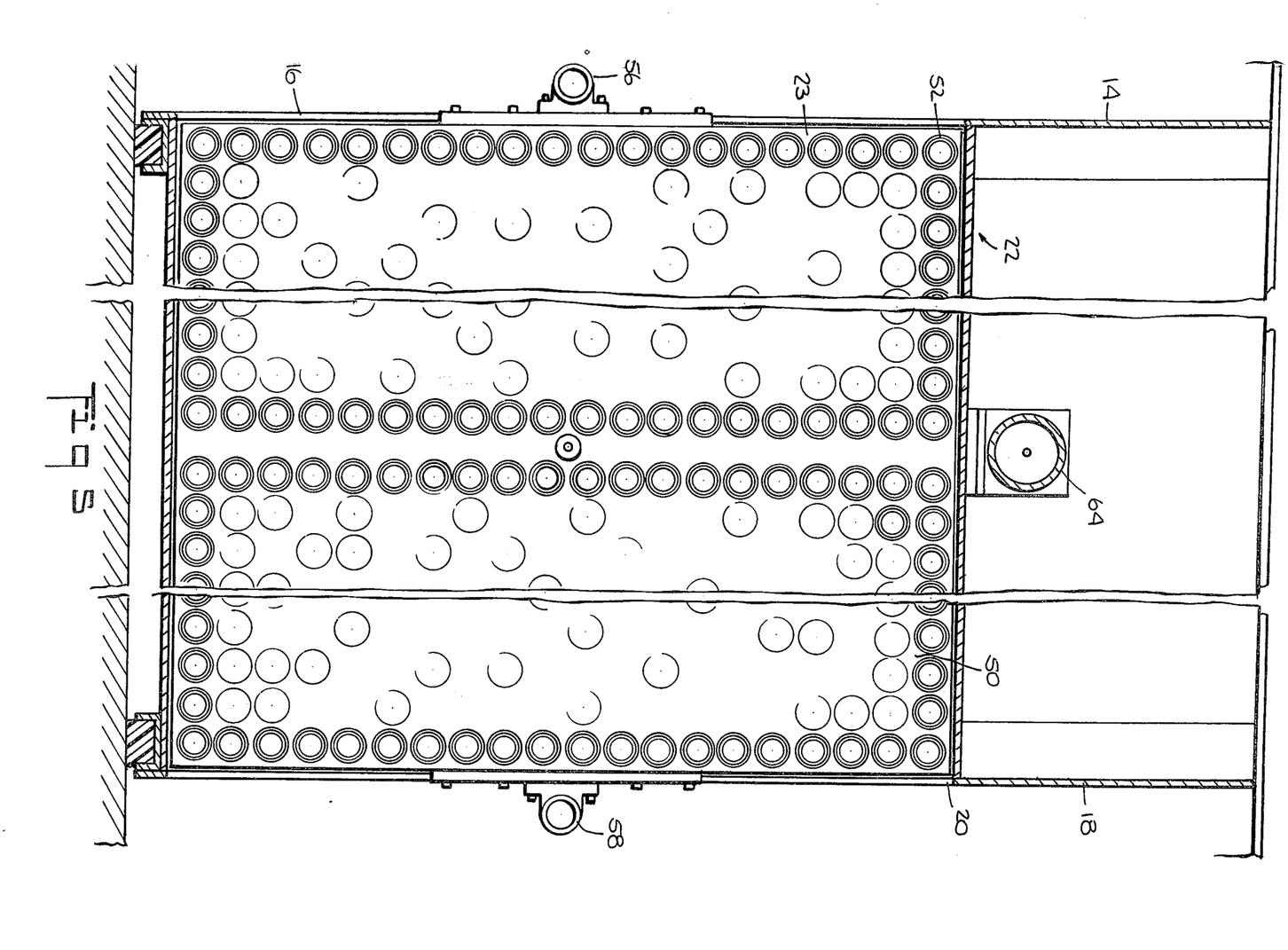
FIG. 5 is a section view taken along lines 5—5 of FIG. 3.

Purification unit 10 is preferably constructed of stainless steel and includes a front baffle 14 formed with an inlet port 16, a rear baffle 18 formed with an outlet port 20, and inner housing or lamp box 22, shown in FIGS. 2 and 4, provided between the baffles to define a fluid passageway 23 between the inlet and outlet ports. Baffles 14 and 18 are dimensioned to extend completely across channel 12 so that all of the waste water is directed through inlet port 16 into the inner housing or lamp box 22 for treatment. As will be explained more fully hereinafter, the transverse width of lamp box 22 is governed by the length of available U.V. lamps. Thus, baffles 14 and 18 are required to adjust the unit to fit the channels in existing treatment facilities and also to maintain a proper water level for full flow through the unit.

Inner housing 22 includes a pair of side plates 24, 26, a top plate 28 and a bottom plate 30 arranged about the periphery of ports 16, 20 and welded or otherwise connected at their edges to each other and to the front and rear baffles 14, 18. As best shown in FIG. 4, side plate 24 is formed with a plurality of spaced-apart apertures arranged in columns and rows. Although not shown, side plate 26 is also formed with a plurality of apertures arranged so that the side plates are mirror images of each other.

Figure 3:
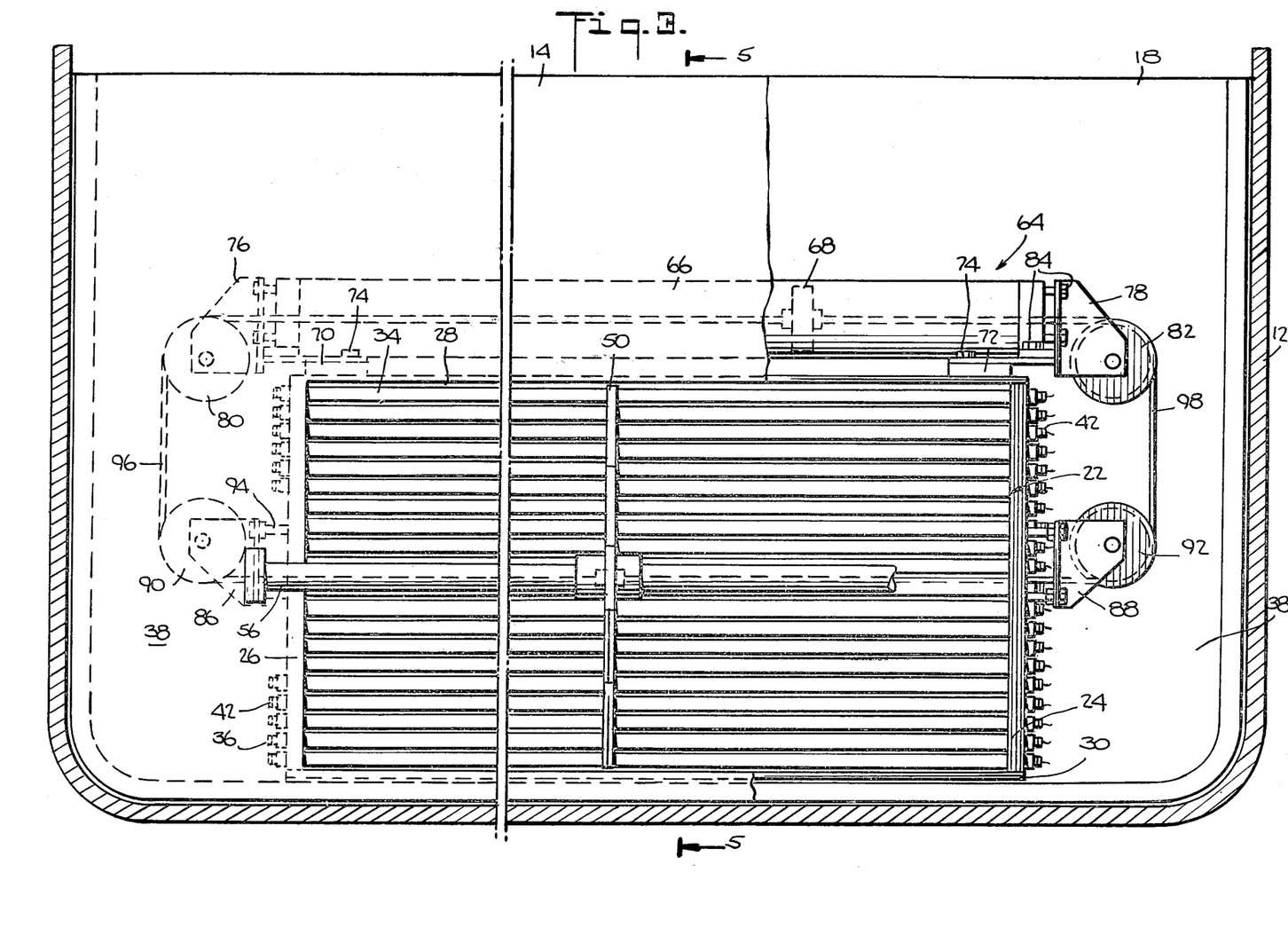
FIG. 3 is an elevational view, partially cut away, of the inlet side of the purification unit of FIG. 1.
Figures 6, 8, 9:
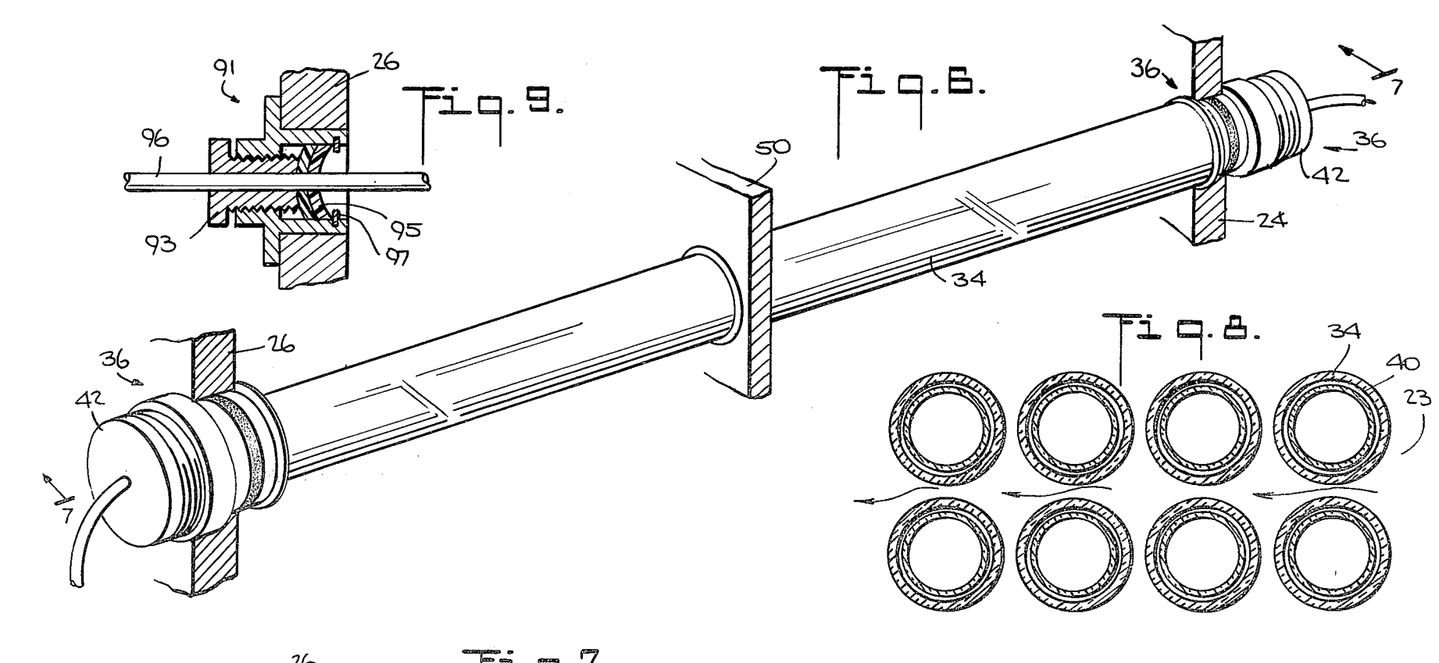
FIG. 6 is an enlarged fragmentary perspective view showing the mounting of a quartz jacket and ultraviolet lamp in the unit of FIG. 1.
FIG. 8 is an enlarged fragmentary section view showing the sheet-like fluid flow past a number of ultraviolet lamps mounted in associated quartz jackets.
FIG. 9 is an enlarged fragmentary section view showing a seal for sealing a cable which passes into the unit of FIG. 1 to reciprocate a wiping plate.
Figure 7:
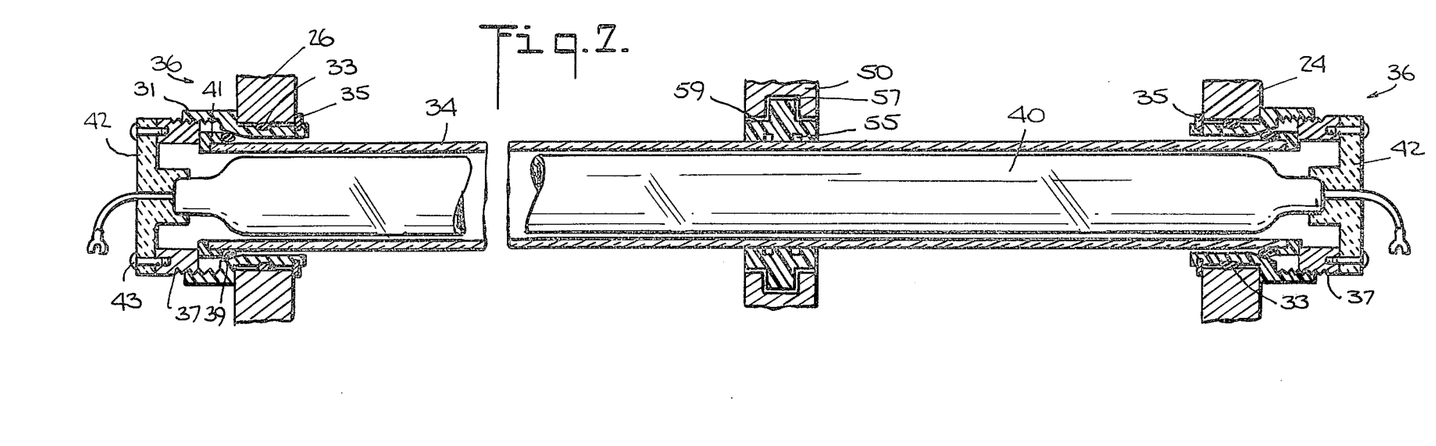
FIG. 7 is a sectional view taken along lines 7—7 of FIG. 6.

A plurality of quartz jackets 34 are mounted between the corresponding apertures 32 in plates 24 and 26 to form parallel columns and rows of jackets which extend transversely across fluid passageway 23. As shown in FIGS. 3, 6 and 7, the opposite ends of each jacket 34 extend into the region 38 outside the inner housing 22 and are supported in the apertures 32 by sealing units 36 to prevent water leakage into region 38 which must be kept dry due to the electrical connections produced therein, as will be explained below.

As best shown in FIG. 7, each sealing unit 36 includes an O-ring support 31 for retaining an O-ring 33 in sealing contact with the associated side wall 24, 26 to prevent leakage into region 38. A snap ring retainer 35 is provided to facilitate replacement of O-ring 33. Since the quartz jacket 34 has a tolerance of ±1 mm, each sealing unit is also adjustable to accomodate this tolerance range. Thus, a threaded end piece 37 is adjustably tightened on the correspondingly threaded outer end of support 31 to force a further O-ring seal 39 against a chamfer in the support 31 by means of a plastic transition piece 41 until sufficient support is achieved. The transition piece also provides protection for the end of the quartz jacket.

Elongated ultraviolet lamps 40 which emit ultraviolet light in the germicidal range are removably mounted concentrically in jackets 34. Ceramic connectors 42 are removably attached to the end pieces 37 by screws 43 and are shaped to assure proper centering of the lamps 40 within the jackets 34. These connectors provide electrical power to the lamps from a power source 44 positioned externally of unit 10. Because of this arrangement, a burnt out lamp can readily be replaced during operation of the unit by merely removing an associated electrical connector 42, sliding the lamp out of its jacket 34 and replacing it with a new lamp. In this regard, the power soure may include individual pilot lights (not shown) for each lamp 40 thus providing a simple indication of lamp failure. In such manner, the unit can be run continuously. Alternatively, lamp replacement may be done during a periodic maintenance check when the unit 10 is removed from channel 12.

In order to provide maximum germicidal kill, the fluid to be treated must be subjected to a predetermined intensity of ultraviolet radiation for a particular dwell time. I have found that intensity is more important than dwell time since high intensity radiation will provide maximum kill of all forms of bacteria with a dwell time of only several seconds. Moreover, intensity is the sole parameter when the fluid to be treated is turbid or colored such as is sometimes the case in waste water treatment. Since intensity diminishes hyperbolically as the distance from the ultraviolet light source is increased, the fluid must be kept close to the source of ultraviolet radiation to assure high intensity exposure.

My invention assures such high intensity exposure by spacing the apertures 32 in side plates 24, 26 so that each jacket is no more than about one half inch away from an adjacent jacket and no more than about one quarter inch, preferably 3/16 inch, from an adjacent top or bottom plate. As a result of this spacing, the waste water assumes a sheet-like flow pattern wherein no portion of the water is more than about one quarter inch away from the surface of a jacket as it flows through passageway 23, as shown in FIG. 8. With this lamp arrangement I have found that a dwell time of as little as two seconds will provide maximum germicidal kill.

I have found that the number of lamps which must be incorporated into unit 10 for proper germicidal effect is a function of the volume flow rate of the secondary waste water effluent. More specifically, I have determined that the number of usable lamp arc inches, per gallon per minute of waste water to be treated should be greater than or equal to three and less than or equal to five. This relationship can be expressed by the following equation:

$$3 \leq X(l)/V \leq 5$$

where X is the number of lamps, l is the usable arc length of the lamps in inches and V is the volume flow rate in gallons per minute. While the upper limit of 5 may be exceeded, there is no material gain in efficiency and energy waste is incurred.

As used herein, the term "usable arc length" means the length in inches of maximum ultraviolet emission along an ultraviolet lamp. For example, the longest commercially available U.V. lamp is presently about 64 inches from end to end. The arc length, i.e. distance between electrodes in such lamp is 60 inches. However, there is a low U.V. emission area of about ½ inch inwardly of each electrode. Thus, the "usable arc length" (l) is 59 inches.

Unit 10, as shown in the drawings, is suitable for treating eight million gallons of waste water per day, or 5,556 gallons per minute with four hundred ultraviolet lamps arranged in a 20 lamp by 20 lamp square, each lamp having a usable arc length of fifty nine inches. Since these parameters define a device having 4.25 lamp inches per gallon per minute, the above equation is satisfied and maximum germicidal kill is assured.

Referring back to FIG. 1, lamps 40 extend horizontally across channel 12. Since the maximum ultraviolet lamp size presently available has a usable arc length of fifty nine inches, the width of the inlet and outlet ports 16, 20 and the distance between side plates 24 and 26 is also limited to fifty nine inches as mentioned above. As shown in FIG. 7, each lamp 40, extends slightly past the side plates 24 and 26 to block out the low emission areas and also to facilitate access to the electrical connections. The height of the inlet and outlet ports and of passageway 23 must then be selected to prevent excessive damming of the secondary waste water effluent and to minimize the head loss across the inlet port. It is preferred that the lamps be arranged in a square matrix which minimizes pressure drop. Thus, in the embodiment shown wherein 400 lamps are utilized, such lamps are positioned in quartz jackets each having a diameter of 0.94 inches. The quartz jackets are, as described above, mounted in apertures 32 in side plates 24 and 26. To provide for the proper fluid thickness between adjacent jackets, the center to center distance between adjacent apertures 32 is 1.41 inches. This configuration yields a total distance between jacket walls of 0.47 inches and thus a maximum light exposure distance of less than one quarter inch. With the top and bottom row of jackets arranged so greater than 3/16 inch from the top and bottom plates respectively, the outside dimensions of the lamp box or housing is 60 inches wide, 30 inches high and 30 inches deep.

While I have shown the lamps and associated jackets in a square matrix and extending horizontally across channel 12, and such a construction is the best mode which I contemplate for my invention, I do not intend to limit the invention to such an arrangement. Thus, the image might also be arranged in a rectangular configuration or vertically, for example.

Since secondary waste water effluent includes suspended particles therein which tend to accumulate, with time, on the outer surfaces of the jackets 34 to block the ultraviolet rays and thereby reduce the killing effect of the unit, I also provide a wiper for removing particulate matter from the lamp jackets. As shown in the drawings, the wiper includes a stainless steel wiping plate 50 formed with a plurality of apertures 52 corresponding to apertures 32 in side plates 24 and 26 so that plate 50 is slidable along jackets 34. As best shown in FIG. 7, an annular elastomeric wiper gland 54 is provided in each aperture 52. The wiper glands are substantially T-shaped in cross-section with the stem of the T situated within an annular groove 57 in aperture 52. A clearance 59 is provided between gland 54 and plate 50 so that the gland 54 floats thus compensating for any irregularity in the quartz jacket 34 which otherwise would cause the quartz to break. The head of the T also includes a pair of annular grooves 55 which enable some fluid to collect between the gland and associated jacket and thereby provide a lubricating effect.

As best shown in FIG. 2, to support wiper plate 50 and enable it to slide along jackets 34 without cocking horizontally or vertically, support bars 56 and 58 are mounted on the front baffle 14 and rear baffle 18, respectively, to extend across the inlet and outlet ports 16 and 20. Sleeves 60 and 62, provided on each support bar, are welded or otherwise connected to the opposite sides of wiper plate 50. It is essential that wiper plate 50 be accurately guided so that the plate 50 does not tend to rest upon the quartz jackets 34 or scrape upon the bottom plate 30 which could cause the quartz jackets to break. Therefore, sleeves 60 and 62 are preferably each provided with a plurality of linear ball bearings (not shown) which insure a frictionless and precise mounting upon support bars 56 and 58.

A pneumatic motor 64 is provided to reciprocate wiper plate 50. The motor includes an elongated cylinder 66 provided with fluid ports at each end (not shown) and a reciprocable piston 68. Cylinder 66 is mounted by means of mounting brackets 70, 72 and bolts 74 to top plate 28 midway between the front and rear baffles 14, 18 and with its longitudinal axis parallel to the lamps 40. Support brackets 76, 78 for rotatably mounting idler pulleys 80, 82 are connected to the end caps of cylinder 66 and to the adjacent mounting brackets 70, 72, respectively, with bolts 84. Additional support brackets 86, 88, for rotatably supporting idler pulleys 90, 92, are mounted to side plates 26, 24 with bolts 94. A stainless steel cable 96 is connected at one end to the left side of piston 68 and extends around pulleys 80 and 90 and through an aperture (FIG. 9) formed at the center of side plate 26 with its other end fastened to the center of the left side of wiper plate 50. A similar cable 98 extends from the right side of piston 68, around pulleys 82 and 92, through side plate 24 to the center of the right side of the wiper plate. All of the idler pulleys have position adjustment to provide cable tensioning. To insure against leakage, a seal 91 is provided in each side plate 24, 26, through which cables 96 and 98 pass. Preferably, as shown in FIG. 9, seal 91 comprises a housing 93 secured by welding or other means to side plate 26 to extend therethrough. Within housing 93, a pair of elastomeric cup seals 95 are held by a snap ring 97 through which cable 96 passes. Of course, other forms of seals may be utilized.

The operation of purification unit 10 which is provided with four hundred ultraviolet lamps for treating eight million gallons of waste water a day, will now be described.

Effluent 13 from a secondary waste water treatment process is directed through channel 12 into the purification unit 10. Because of the close spacing of jackets 34, the water assumes a sheet-like flow pattern and is never more than about a quarter inch away from a jacket. As a result, high intensity ultraviolet radiation from lamps 40 which are simultaneously driven by a power source 44 kills substantially all forms of bacteria in the water.

As the water is being treated, pneumatic motor 64 is operated by alternately supplying pressurized air to one side of piston 68 while the opposite side is exhausted by means of a conventional switching valve (not shown). Motor 64 in turn causes wiper plate 50 to reciprocate and remove solid material which has built up on the quartz jackets. The wiper plate 50 may be moved at any desired speed or frequency. Preferably, however, a stroke frequency control (not shown) ranging from seconds to hours is provided for altering the stroke frequency in accordance with the suspended solids in the influent. Under normal conditions in a test installation of the unit described above, a longitudinal sweep every ten minutes was found optimal. When not in use, wiper plate 50 is preferably maintained flush against an end plate.

Power supply 44 for the U.V. lamps is of standard design. In the embodiment described above using 400 lamps, a 40 KW power source is used with an operational voltage of 480. The save on power consumption, controls are provided to shut off groups of lamps or to vary the power supplied to the entire matrix of lamps or portions thereof. Thus, the power supplied to the lamps or number of lamps energized can be varied according to the fluid volume passing through the unit and suspended solids in the influent. As these two parameters change frequently in waste treatment facilities, the ability to control the power supplied to the lamps substantially reduces costs without effecting bacterial kill capabilities.

In the following Table 1, test results are given illustrating the disinfectant ability of an experimental unit as described above installed in an operating waste water treatment facility.

TABLE 1

| Fecal Coliform Counts (a) | | Percent | Influent |
|---|---|---|---|
| Influent | Effluent | Power to Unit (b) | Suspended Solids, mg/L |
| 6.0-mgd Flow Rate | | | |
| 52,250 | 7 | 100 | 23 |
| 69,500 | 13 | 100 | 17 |
| 190,000 | 17 | 100 | 25 |
| 100,000 | 11 | 100 | 17 |
| 93,000 | 14 | 100 | 24 |
| 13,000 | 12 | 100 | 12 |
| 9,000 | 4 | 100 | 10 |
| 57,000 | 13 | 100 | 15 |
| 40,000 | 32 | 100 | 15 |
| 23,000 | 28 | 100 | 7 |
| 29,000 | 90 | 35 | 7 |
| 29,000 | 24 | 100 | 6 |
| 29,000 | 130 | 40 | 7 |
| 6.5-mgd Flow Rate | | | |
| 239,000 | 79 | 100 | 6 |
| 307,000 | 36 | 100 | 7 |
| 22,000 | 40 | 100 | 3 |
| 7.0-mgd Flow Rate | | | |
| 76,500 | 17 | 100 | 7 |
| 16,000 | 323 | 40 | 7 |
| 560,000 | 90 | 100 | 18 |
| 25,000 | 14 | 100 | 8 |
| 7.5-mgd Flow Rate | | | |
| 155,000 | 6 | 100 | 20 |
| 46,000 | 28 | 100 | 15 |
| 11,000 | 26 | 100 | 10 |

TABLE 1-continued

| Fecal Coliform Counts (a) | | Percent | Influent |
|---|---|---|---|
| Influent | Effluent | Power to Unit (b) | Suspended Solids, mg/L |
| 11,000 | 345 | 50 | 10 |
| 15,000 | 13 | 100 | 9 |

(a) Colonies per 100 ml by membrane filter method
(b) Power variation was for test purposes The foregoing test results illustrate that the present invention effectively reduces fecal coliform to levels well below present standards of 400 per 100 ml for a seven day average and 200 per 100 ml for 30 days as specified by the National Pollutant Discharge Elimination System permit. The foregoing results also indicate disinfection well within the up-graded requirements of 100 per 100 ml, now under consideration.

While the nature of the action is not presently understood, I have found that treatment of waste water with a unit such as described above improves the clarity of the effluent which is an unexpected development. Preliminary tests have also indicated a potential viricidal capability.

While I have disclosed a single preferred embodiment, it must be recognized that various modifications may be made without departing from the invention. For example, while I have disclosed a pneumatic motor, any type of motor such as a hydraulic motor which will reciprocate the wiper plate may be utilized. Similarly, instead of two separate cables, a single cable fastened at its ends to opposite sides of the piston and passing through the wiper plate, or vice versa, is also contemplated. Finally, the inner housing with the jackets, wiper plate and motor may be constructed as a separate unit with the baffles, shaped for the particular channel in which the unit is to be used, subsequently welded at each end of the housing.

Moreover, while I have described a unit having 400 lamps suitable for disinfecting an average daily fluid flow of around 8 million gallons, larger or smaller units may be constructed using the equation set forth above. For example, a unit suitable for handling a 4 million gallon per day flow would consist of 256 lamps arranged in a 24"×24"×60" lamp box or unit and powered by a 25.6 KW power source. On the other hand, to treat 15 million gallons per day, one would use 676 lamps arranged in a 42"×42"×60" lamp box or unit and powered by a 67.6 KW power source.

In summary, my invention provides a highly efficient and economical method and apparatus for purifying large quantities of waste water by means of ultraviolet radiation. Because I have determined the number of lamps needed for a particular volume rate of flow and have closely spaced the lamps, a maximum kill rate of virtually all forms of bacteria is assured. The effective use of ultraviolet radiation for commercial sewage treatment made possible by my invention also eliminates the need for chlorination and dechlorination processes, the production of carcinogens and the cost associated with the hoists, scales, pumps and similar equipment required with such processes.

What is claimed is:

1. Apparatus for treating secondary waste water effluent with ultraviolet light comprising: a housing shaped to define a fluid passageway therethrough between an inlet and an outlet formed at opposite ends thereof; a plurality of elongated cylindrical, light emitting jackets mounted in parallel within said housing to extend transversely across said fluid passageway; a plurality of elongated ultraviolet lamps removably and concentrically mounted within said jackets; means for supplying electrical power to operate said ultraviolet lamps; a plate mounted within said housing perpendicularly to the longitudinal axes of said jackets, said plate having apertures through which said jackets extend; wiper glands positioned within each aperture between said plate and the associated jacket; a fluid driven piston mounted exteriorally to said housing; at least one cable connecting said piston to the opposite faces of said plate whereby said plate may be reciprocated lengthwise of said jackets to clean said jackets; and guide means associated with said plate to prevent cocking thereof when reciprocated.

2. Apparatus for treating secondary waste water effluent with ultraviolet light comprising a housing shaped to define a fluid passageway therethrough between an inlet and an outlet formed at opposite ends thereof, a plurality of elongated, cylindrical, light emitting jackets mounted in parallel within said housing to extend transversely across the fluid passageway, adjacent jackets being spaced less than about one half inch apart so that none of the waste water is more than about one quarter inch away from a jacket as it flows through the housing, a plurality of elongated ultraviolet lamps of equal usable arc length removably and concentrically mounted within said jackets, wherein the number of lamps and associated jackets satisfies the equation:

$$3 \leq X(l)/V \leq 5$$

where X is the number of lamps, l is the usable arc length of each lamp in inches and V is the volume flow rate of the waste water in gallons per minute; means for supplying electrical power to operate said ultraviolet lamps; a wiper plate mounted within said housing perpendicular to the longitudinal axes of said jackets, said wiper plate having apertures through which said jackets extend, and annular wiper glands positioned within each aperture between said plate and the associated jacket; a motor mounted exteriorly of said housing; and cable means arranged between said motor and said wiper plate to reciprocate said wiper plate lengthwise of said jackets.

3. Apparatus according to claim 2, wherein said apparatus further comprises baffle means for directing said waste water to be treated through said passageway.

4. Apparatus according to claim 2 wherein said motor is an hydraulically driven piston.

5. Apparatus according to claim 2 wherein the dimension of said fluid passageway in the direction of the longitudinal axes of said jackets corresponds to the usuable arc length of said ultraviolet lamps.

6. Apparatus according to claim 2 wherein said motor is a pneumatically driven piston.

7. Apparatus according to claim 6 wherein said cable means comprises a pair of cables each connecting an end of said piston to the corresponding face of said wiper plate, and said housing includes means for guiding said cables from said piston to said plate.

8. Apparatus according to claim 7 wherein said guide means are idler pulleys.

9. Apparatus according to claim 2 further including support means adapted to support and prevent said wiper plate from cocking when reciprocated.

10. Apparatus according to claim 9 wherein said support means comprises a support bar mounted exteriorly to each of the opposite faces of said housing and means for slidably connecting the sides of said wiper plate to each of said support bars.

11. Apparatus according to claim 10 wherein said means for slidably connecting said wiper plate to each of said support bars are sleeves positioned on said bars and rigidly connected to said wiper plate.

12. Apparatus for treating secondary waste water effluent with ultraviolet light comprising front and rear baffles each dimensioned to extend completely across the flow path of the waste water and defining an inlet port and outlet port, respectively, a housing between said baffles shaped to define a fluid passageway between the inlet and outlet ports, a plurality of elongated, cylindrical quartz jackets extending transversely in rows and columns across said passageway and sealingly mounted at their opposite ends to said housing, adjacent jackets being spaced less than about one half inch apart so that none of the waste water is more than about one quarter inch away from a jacket as it flows through said housing, a plurality of elongated ultraviolet lamps of equal usuable arc length removably and concentrically mounted within said jackets, wherein the number of lamps and associated jackets satisfies the equation:

$$3 \leq X(l)/V \leq 5$$

wherein X is the number of lamps, l is the usable arc length of each lamp in inches and V is the volume flow rate of the waste water in gallons per minute, means for supplying electrical power to said lamps, a wiper plate formed with a plurality of apertures and mounted for sliding movement along the outer surfaces of said jackets, a plurality of annular wiper glands mounted in said apertures to surround said jackets, means for reciprocating said wiper plate lengthwise of said jackets comprising a pneumatically driven piston connected by cable to the opposite faces of said wiper plate; a pair of support bars, one mounted horizontally to said front baffle and the other mounted horizontally to said rear baffle; and means slidably connecting said plate to said support bars to prevent cocking of said plate when reciprocated.

* * * * *